US008497337B2

(12) United States Patent
Herfert et al.

(10) Patent No.: US 8,497,337 B2

(45) Date of Patent: Jul. 30, 2013

(54) PROCESS FOR PRODUCING WATER-ABSORBING POLYMER PARTICLES WITH IMPROVED COLOR STABILITY

(75) Inventors: Norbert Herfert, Altenstadt (DE); Thomas Daniel, Waldsee (DE)

(73) Assignee: BASF SE, Ludwigshafen (DE)

( * ) Notice: Subject to any disclaimer, the term of this patent is extended or adjusted under 35 U.S.C. 154(b) by 210 days.

(21) Appl. No.: 12/946,602

(22) Filed: Nov. 15, 2010

(65) Prior Publication Data

US 2011/0121230 A1 May 26, 2011

Related U.S. Application Data

(60) Provisional application No. 61/263,419, filed on Nov. 23, 2009.

(51) Int. Cl.

*C08F 220/06* (2006.01)
*C08K 5/07* (2006.01)
*C08K 5/05* (2006.01)
*C08K 5/24* (2006.01)
*C08K 5/29* (2006.01)

(52) U.S. Cl.

USPC ............ 526/317.1; 526/72; 526/89; 526/100; 524/115; 524/126; 524/237; 524/354; 524/366

(58) Field of Classification Search

USPC .................. 526/89, 317.1, 100, 72; 524/354, 524/366, 115, 126, 237

See application file for complete search history.

(56) References Cited

U.S. PATENT DOCUMENTS

| | | | | |
|---|---|---|---|---|
| 5,610,208 | A * | 3/1997 | Dairoku et al. | 525/384 |
| 7,179,875 | B2 | 2/2007 | Fuchs et al. | |
| 7,714,061 | B2 | 5/2010 | Riegel et al. | |
| 7,737,231 | B2 * | 6/2010 | Handa et al. | 526/78 |
| 2003/0135172 | A1 * | 7/2003 | Whitmore et al. | 604/359 |
| 2010/0041550 | A1 | 2/2010 | Riegel et al. | |
| 2010/0286287 | A1 | 11/2010 | Walden | |
| 2011/0118114 | A1 | 5/2011 | Riegel et al. | |
| 2011/0136986 | A1 | 6/2011 | Elliott et al. | |

FOREIGN PATENT DOCUMENTS

| | | | |
|---|---|---|---|
| JP | 2000327926 | A * | 11/2000 |
| WO | WO-00/55245 | A1 | 9/2000 |
| WO | WO-03/014172 | A2 | 2/2003 |
| WO | WO 2004/084962 | A1 | 10/2004 |
| WO | WO-2006/058682 | A1 | 6/2006 |
| WO | WO-2008/092842 | A1 | 8/2008 |
| WO | WO-2008/092843 | A1 | 8/2008 |
| WO | WO-2009/060062 | A1 | 5/2009 |
| WO | WO-2010/012762 | A2 | 2/2010 |
| WO | WO-2010/018143 | A1 | 2/2010 |
| WO | WO-2011/032876 | A1 | 3/2011 |

OTHER PUBLICATIONS

JP 2000-327926, Derwent Ab., Nov. 2000.*

Buchholz et al. (eds.), Modern Superabsorbent Polymer Technology, Wiley-VCH, pp. 71-103 (1998).

* cited by examiner

*Primary Examiner* — Satya Sastri

(74) *Attorney, Agent, or Firm* — Marshall, Gerstein & Borun LLP

(57) ABSTRACT

A process for producing water-absorbing polymer particles, wherein at least one aliphatic aldehyde or reaction product thereof with an aliphatic alcohol, an aliphatic amine, ammonia, a hypophosphite or a phosphite is added.

14 Claims, No Drawings

PROCESS FOR PRODUCING WATER-ABSORBING POLYMER PARTICLES WITH IMPROVED COLOR STABILITY

CROSS-REFERENCE TO RELATED APPLICATIONS

This application claims the benefit of U.S. provisional patent application No. 61/263,419, filed Nov. 23, 2010, incorporated herein by reference in its entirety.

The present invention relates to processes for producing water-absorbing polymer particles, wherein at least one aliphatic aldehyde or reaction product thereof with an aliphatic alcohol, aliphatic amine, ammonia, a hypophosphite or a phosphite is added, and to the water-absorbing polymer particles obtainable by the process according to the invention.

Water-absorbing polymer particles are used to produce diapers, tampons, sanitary napkins and other hygiene articles, but also as water-retaining agents in market gardening. The water-absorbing polymer particles are also referred to as superabsorbents.

The production of water-absorbing polymer particles is described in the monograph "Modern Superabsorbent Polymer Technology", F. L. Buchholz and A. T. Graham, Wiley-VCH, 1998, pages 71 to 103.

The properties of the water-absorbing polymer particles can be adjusted, for example, via the amount of crosslinker used. With increasing amount of crosslinker, the centrifuge retention capacity (CRC) falls and the absorption under a pressure of 21.0 g/cm$^2$ (AUL0.3 psi) passes through a maximum.

To improve the application properties, for example permeability of the swollen gel bed (SFC) in the diaper and absorption under a pressure of 49.2 g/cm$^2$ (AUL0.7 psi), water-absorbing polymer particles are generally surface postcrosslinked. This increases the degree of crosslinking of the particle surface, which allows the absorption under a pressure of 49.2 g/cm$^2$ (AUL0.7 psi) and the centrifuge retention capacity (CRC) to be at least partly decoupled. This surface postcrosslinking can be performed in the aqueous gel phase. Preferably, however, dried, ground and screened-off polymer particles (base polymer) are surface coated with a surface postcrosslinker, thermally surface postcrosslinked and dried. Crosslinkers suitable for this purpose are compounds which can form covalent bonds with at least two carboxylate groups of the water-absorbing polymer particles.

A problem which often occurs in water-absorbing polymer particles is that of discoloration, which occurs in the course of storage at elevated temperature or elevated air humidity. Such conditions often occur in the course of storage in tropical or subtropical countries. Under such conditions, water-absorbing polymer particles tend to yellow; they may even take on a brown or even almost black color. This discoloration of the actually colorless water-absorbing polymer particles is unsightly and undesired, since it is visible especially in the desired thin hygiene products, and consumers reject unsightly hygiene products. The cause of the discoloration has not been entirely clarified, but reactive compounds such as residual monomers from the polymerization, the use of some initiators, impurities in the monomers or in the neutralizing agent, surface postcrosslinkers or stabilizers in the monomers used appear to play a role.

According to WO 00/55245 A1, the color stability of water-absorbing polymer particles can be improved by adding inorganic reducing agents. The inorganic reducing agents can be added, for example, to the polymer gel after the polymerization, or after the thermal surface postcrosslinking.

WO 2006/058682 A1 teaches that the presence of oxygen in the thermal surface postcrosslinking leads to discoloration.

According to WO 2004/084962 A1, the use of sulfinic acids as polymerization initiators has a favorable effect on the color stability of the water-absorbing polymer particles obtained.

WO 2008/092842 A1 and WO 2008/092843 A1 disclose coating with basic salts for the same purpose.

According to WO 2009/060062 A1, the color stability of water-absorbing polymer particles with sulfonic acids and salts thereof can be increased, in which case the sulfonic acids or salts thereof are preferably added directly before the surface postcrosslinking.

WO 03/014172 A2 describes a process for producing water-absorbing polymer particles, wherein the acrylic acid used has been treated beforehand with an aldehyde scavenger, since the presence of aldehydes in particular is said to lead to discoloration.

It was an object of the present invention to provide a process for producing water-absorbing polymer particles with improved color stability. At the same time, the water-absorbing polymer particles, especially in the course of prolonged storage in a warm and moist environment, should not develop any unpleasant odors.

The object is achieved by a process for producing water-absorbing polymer particles by polymerizing a monomer solution or suspension comprising a) at least one ethylenically unsaturated monomer which bears acid groups and may be at least partly neutralized,
b) at least one crosslinker,
c) at least one initiator,
d) optionally one or more ethylenically unsaturated monomers copolymerizable with the monomers mentioned under a) and
e) optionally one or more water-soluble polymers, comprising the steps of polymerizing the monomer solution to give a polymer gel i), optionally comminuting the resulting polymer gel ii), drying the polymer gel iii), grinding and classifying the dried polymer gel to polymer particles iv), and optionally thermally surface postcrosslinking the classified polymer particles v), which comprises adding at least one aliphatic aldehyde or reaction product thereof with an aliphatic alcohol, an aliphatic amine, ammonia, a hypophosphite or a phosphite before, during or after one of steps i) to v).

The aliphatic aldehyde or reaction product thereof with an aliphatic alcohol, an aliphatic amine, ammonia, a hypophosphite or a phosphite is preferably added after step iv) and before, during or after step v). The aliphatic aldehyde or reaction product thereof with an aliphatic alcohol, an aliphatic amine, ammonia, a hypophosphite or a phosphite is most preferably added after step v).

Aliphatic aldehydes, alcohols and amines in the context of this invention are compounds which have no aromatic rings or ring systems in their structures. The aldehydes usable in accordance with the invention also comprise di- and polyfunctional aldehydes.

The aliphatic aldehydes used are preferably $C_1$- to $C_5$-aldehydes, more preferably $C_1$- to $C_4$-aldehydes, especially preferably $C_1$- to $C_3$-aldehydes, very especially preferably $C_2$- to $C_3$-aldehydes.

Suitable aliphatic aldehydes are formaldehyde, acetaldehyde, propionaldehyde, butyraldehyde, glycolaldehyde, glyceraldehyde and glyoxylic acid.

Very particularly preferred aliphatic aldehydes are glyoxylic acid and salts thereof, for example sodium glyoxylate and potassium glyoxylate.

Suitable reaction products of the aliphatic aldehydes with aliphatic alcohols are hemiacetals and acetals.

Suitable hemiacetals are dimeric α-hydroxy aldehydes such as 2,5-dihydroxy-1,4-dioxane, 3,6-dihydroxy-2,5-dihydroxymethyl-1,4-dioxane. The hemiacetals form here as a result of addition of the hydroxyl group of one α-hydroxy aldehyde onto the aldehyde group of the other α-hydroxy aldehyde, i.e. the α-hydroxy aldehyde is simultaneously the aliphatic aldehyde and aliphatic alcohol.

Suitable acetals are the acetals of formaldehyde, acetaldehyde, propionaldehyde, butyraldehyde, glycolaldehyde, glyceraldehyde and glyoxylic acid.

Very particularly preferred acetals are the acetals of glyoxylic acid and salts thereof, such as sodium 2,2-dimethoxyacetate, potassium 2,2-dimethoxyacetate, sodium 2,2-diethoxyacetate and potassium 2,2-diethoxyacetate.

Suitable reaction products of the aliphatic aldehydes with aliphatic amines are azomethines, enamines and aminals. Azomethines formed from aliphatic aldehydes and aliphatic amines polymerize readily and can also be used in polymeric form.

The reaction products of the aliphatic aldehydes with ammonia can likewise polymerize. For instance, the reaction product of acetalaldehyde and ammonia is present in the form of the trimer. The corresponding reaction product of formaldehyde and ammonia reacts with further formaldehyde to give hexamethylenetetramine.

Suitable reaction products of the aliphatic aldehydes with hypophosphites and phosphites are phosphinic acids and phosphonic acids.

Very particularly preferred phosphinic acids and phosphonic acids are 2-hydroxy-2-phosphinoacetic acid and 2-hydroxy-2-phosphonoacetic acid, and salts thereof.

The use amount of aliphatic aldehyde or the reaction product thereof with an aliphatic alcohol, an aliphatic amine, ammonia, a hypophosphite or a phosphite, based on the water-absorbing polymer particles, is preferably from 0.001 to 2% by weight, more preferably from 0.005 to 1% by weight, most preferably from 0.01 to 0.5% by weight.

The present invention is based on the finding that aliphatic aldehydes, i.e. aldehydes which have no aromatic rings or ring systems, significantly reduce the discoloration tendency of water-absorbing polymer particles in a warm and moist environment. In this context, the aliphatic aldehydes need not themselves be used. It is also possible to use compounds from which the desired aliphatic aldehydes can be released readily. Such compounds are, for example, the reaction products of aliphatic aldehydes with aliphatic alcohols, aliphatic amines, ammonia, hypophosphites or phosphites.

Although saccharides, disaccharides and polysaccharides are also present in the form of hemiacetals, they are less suitable for the process according to the invention since they themselves tend to discolor, especially under thermal stress.

Although the sulfinic acids described in WO 2004/058682 A1 can suppress yellowing, they tend to form unpleasant odors.

In a preferred embodiment of the present invention, a sulfite is additionally added. The sulphite can likewise be added before, during or after one of steps i) to v), and irrespective of the addition of the aliphatic aldehyde or reaction product thereof with an aliphatic alcohol, an aliphatic amine, ammonia, a hypophosphite or a phosphite.

The sulfite is preferably added after step iv) and before, during or after step v). The aliphatic aldehyde or reaction product thereof with an aliphatic alcohol, an aliphatic amine, ammonia, a hypophosphite or a phosphite is mostly preferably added after step v).

Suitable sulphites are sodium hydrogensulfite and potassium hydrogensulfite. The use amount of sulfite, based on the water-absorbing polymer particles, is preferably from 0.001 to 5% by weight, more preferably from 0.005 to 2% by weight, most preferably from 0.01 to 1% by weight.

The addition of sulfites can further suppress the discoloration tendency of water-absorbing polymer particles.

The production of the water-absorbing polymer particles is explained in detail hereinafter:

The water-absorbing polymer particles are produced by polymerizing a monomer solution or suspension and are typically water-insoluble.

The monomers a) are preferably water-soluble, i.e. the solubility in water at 23° C. is typically at least 1 g/100 g of water, preferably at least 5 g/100 g of water, more preferably at least 25 g/100 g of water, most preferably at least 35 g/100 g of water.

Suitable monomers a) are, for example, ethylenically unsaturated carboxylic acids, such as acrylic acid, methacrylic acid and itaconic acid. Particularly preferred monomers are acrylic acid and methacrylic acid. Very particular preference is given to acrylic acid.

Further suitable monomers a) are, for example, ethylenically unsaturated sulfonic acids, such as styrenesulfonic acid and 2-acrylamido-2-methylpropanesulfonic acid (AMPS).

Impurities can have a considerable influence on the polymerization. The raw materials used should therefore have a maximum purity. It is therefore often advantageous to specially purify the monomers a). Suitable purification processes are described, for example, in WO 2002/055469 A1, WO 2003/078378 A1 and WO 2004/035514 A1. A suitable monomer a) is, for example, acrylic acid purified according to WO 2004/035514 A1 comprising 99.8460% by weight of acrylic acid, 0.0950% by weight of acetic acid, 0.0332% by weight of water, 0.0203% by weight of propionic acid, 0.0001% by weight of furfurals, 0.0001% by weight of maleic anhydride, 0.0003% by weight of diacrylic acid and 0.0050% by weight of hydroquinone monomethyl ether.

The proportion of acrylic acid and/or salts thereof in the total amount of monomers a) is preferably at least 50 mol %, more preferably at least 90 mol %, most preferably at least 95 mol %.

The monomers a) typically comprise polymerization inhibitors, preferably hydroquinone monoethers, as storage stabilizers.

The monomer solution comprises preferably up to 250 ppm by weight, preferably at most 130 ppm by weight, more preferably at most 70 ppm by weight, preferably at least 10 ppm by weight, more preferably at least 30 ppm by weight, especially around 50 ppm by weight, of hydroquinone monoether, based in each case on the unneutralized monomer a). For example, the monomer solution can be prepared by using an ethylenically unsaturated monomer bearing acid groups with an appropriate content of hydroquinone monoether.

Preferred hydroquinone monoethers are hydroquinone monomethyl ether (MEHQ) and/or alpha-tocopherol (vitamin E).

Suitable crosslinkers b) are compounds having at least two groups suitable for crosslinking. Such groups are, for example, ethylenically unsaturated groups which can be polymerized free-radically into the polymer chain, and functional groups which can form covalent bonds with the acid groups of the monomer a). In addition, polyvalent metal salts which can form coordinate bonds with at least two acid groups of the monomer a) are also suitable as crosslinkers b).

Crosslinkers b) are preferably compounds having at least two polymerizable groups which can be polymerized free-radically into the polymer network. Suitable crosslinkers b) are, for example, ethylene glycol dimethacrylate, diethylene glycol diacrylate, polyethylene glycol diacrylate, allyl methacrylate, trimethylolpropane triacrylate, triallylamine, tetraallylammonium chloride, tetraallyloxyethane, as described in EP 0 530 438 A1, di- and triacrylates, as described in EP 0 547 847 A1, EP 0 559 476 A1, EP 0 632 068 A1, WO 93/21237 A1, WO 2003/104299 A1, WO 2003/104300 A1, WO 2003/104301 A1 and DE 103 31 450 A1, mixed acrylates which, as well as acrylate groups, comprise further ethylenically unsaturated groups, as described in DE 103 31 456 A1 and DE 103 55 401 A1, or crosslinker mixtures, as described, for example, in DE 195 43 368 A1, DE 196 46 484 A1, WO 90/15830 A1 and WO 2002/032962 A2.

Preferred crosslinkers b) are pentaerythrityl triallyl ether, tetraalloxyethane, methylenebismethacrylamide, 15-tuply ethoxylated trimethylolpropane triacrylate, polyethylene glycol diacrylate, trimethylolpropane triacrylate and triallylamine.

Very particularly preferred crosslinkers b) are the polyethoxylated and/or -propoxylated glycerols which have been esterified with acrylic acid or methacrylic acid to give di- or triacrylates, as described, for example, in WO 2003/104301 A1. Di- and/or triacrylates of 3- to 10-tuply ethoxylated glycerol are particularly advantageous. Very particular preference is given to di- or triacrylates of 1- to 5-tuply ethoxylated and/or propoxylated glycerol. Most preferred are the triacrylates of 3- to 5-tuply ethoxylated and/or propoxylated glycerol, especially the triacrylate of 3-tuply ethoxylated glycerol.

The amount of crosslinker b) is preferably 0.05 to 1.5% by weight, more preferably 0.1 to 1% by weight, most preferably 0.3 to 0.6% by weight, based in each case on monomer a). With rising crosslinker content, the centrifuge retention capacity (CRC) falls and the absorption under a pressure of 21.0 g/cm$^2$ passes through a maximum.

The initiators c) used may be all compounds which generate free radicals under the polymerization conditions, for example thermal initiators, redox initiators, photoinitiators. Suitable redox initiators are sodium peroxodisulfate/ascorbic acid, hydrogen peroxide/ascorbic acid, sodium peroxodisulfate/sodium bisulfite and hydrogen peroxide/sodium bisulfite. Preference is given to using mixtures of thermal initiators and redox initiators, such as sodium peroxodisulfate/hydrogen peroxide/ascorbic acid. The reducing component used is, however, preferably the disodium salt of 2-hydroxy-2-sulfonatoacetic acid or a mixture of the disodium salt of 2-hydroxy-2-sulfinatoacetic acid, the disodium salt of 2-hydroxy-2-sulfonatoacetic acid and sodium bisulfite. Such mixtures are obtainable as Brüggolite® FF6 and Brüggolite® FF7 (Brüggemann Chemicals; Heilbronn; Germany).

Ethylenically unsaturated monomers d) copolymerizable with the ethylenically unsaturated monomers a) bearing acid groups are, for example, acrylamide, methacrylamide, hydroxyethyl acrylate, hydroxyethyl methacrylate, dimethylaminoethyl methacrylate, dimethylaminoethyl acrylate, dimethylaminopropyl acrylate, diethylaminopropyl acrylate, dimethylaminoethyl methacrylate, diethylaminoethyl methacrylate.

The water-soluble polymers e) used may be polyvinyl alcohol, polyvinylpyrrolidone, starch, starch derivatives, modified cellulose, such as methylcellulose or hydroxyethylcellulose, gelatin, polyglycols or polyacrylic acids, preferably starch, starch derivatives and modified cellulose.

Typically, an aqueous monomer solution is used. The water content of the monomer solution is preferably from 40 to 75% by weight, more preferably from 45 to 70% by weight, most preferably from 50 to 65% by weight. It is also possible to use monomer suspensions, i.e. monomer solutions with excess monomer a), for example sodium acrylate. With rising water content, the energy requirement in the subsequent drying rises, and, with falling water content, the heat of polymerization can only be removed inadequately.

For optimal action, the preferred polymerization inhibitors require dissolved oxygen. The monomer solution can therefore be freed of dissolved oxygen before the polymerization by inertization, i.e. flowing an inert gas through, preferably nitrogen or carbon dioxide. The oxygen content of the monomer solution is preferably lowered before the polymerization to less than 1 ppm by weight, more preferably to less than 0.5 ppm by weight, most preferably to less than 0.1 ppm by weight.

In process step i), the monomer solution or suspension is polymerized. Suitable reactors are, for example, kneading reactors or belt reactors. In the kneader, the polymer gel formed in the polymerization of an aqueous monomer solution or suspension is comminuted continuously by, for example, contrarotatory stirrer shafts, as described in WO 2001/038402 A1. Polymerization on a belt is described, for example, in DE 38 25 366 A1 and U.S. Pat. No. 6,241,928. Polymerization in a belt reactor forms a polymer gel, which has to be comminuted in a further process step ii), for example in an extruder or kneader.

To improve the drying properties, the comminuted polymer gel obtained by means of a kneader can additionally be extruded.

However, it is also possible to dropletize an aqueous monomer solution and to polymerize the droplets obtained in a heated carrier gas stream. This allows the process steps of polymerization i) and drying ii) to be combined, as described in WO 2008/040715 A2 and WO 2008/052971 A1.

The acid groups of the resulting polymer gels have typically been partially neutralized. Neutralization is preferably carried out at the monomer stage. This is typically done by mixing in the neutralizing agent as an aqueous solution or preferably also as a solid. The degree of neutralization is preferably from 25 to 95 mol %, more preferably from 30 to 80 mol %, most preferably from 40 to 75 mol %, for which the customary neutralizing agents can be used, preferably alkali metal hydroxides, alkali metal oxides, alkali metal carbonates or alkali metal hydrogencarbonates and also mixtures thereof. Instead of alkali metal salts, it is also possible to use ammonium salts. Particularly preferred alkali metals are sodium and potassium, but very particular preference is given to sodium hydroxide, sodium carbonate or sodium hydrogencarbonate and also mixtures thereof. However, it is also possible to carry out neutralization after the polymerization, at the stage of the polymer gel formed in the polymerization. It is also possible to neutralize up to 40 mol %, preferably 10 to 30 mol % and more preferably 15 to 25 mol % of the acid groups before the polymerization by adding a portion of the neutralizing agent actually to the monomer solution and setting the desired final degree of neutralization only after the polymerization, at the polymer gel stage. When the polymer gel is neutralized at least partly after the polymerization, the polymer gel is preferably comminuted mechanically, for example by means of an extruder, in which case the neutralizing agent can be sprayed, sprinkled or poured on and then carefully mixed in. To this end, the gel mass obtained can be repeatedly extruded for homogenization.

In process step iii), the resulting polymer gel is dried. The driers are not subject to any restriction. The drying of the polymer gel is, however, preferably carried out with a belt drier until the residual moisture content is preferably 0.5 to 15% by weight, more preferably 1 to 10% by weight, most preferably 2 to 8% by weight, the residual moisture content being determined by EDANA recommended test method No. WSP 230.2-05 “Moisture Content”. In the case of too high a residual moisture content, the dried polymer gel has too low a glass transition temperature $T_g$ and can be processed further only with difficulty. In the case of too low a residual moisture content, the dried polymer gel is too brittle and, in the subsequent comminution steps, undesirably large amounts of polymer particles with an excessively low particle size (“fines”) are obtained. The solids content of the gel before the drying is preferably from 25 to 90% by weight, more preferably from 35 to 70% by weight, most preferably from 40 to 60% by weight. Optionally, it is, however, also possible to use a fluidized bed drier or a paddle drier for the drying operation.

In process step iv), the dried polymer gel is ground and classified, and the apparatus used for grinding may typically be single- or multistage roll mills, preferably two- or three-stage roll mills, pin mills, hammer mills or vibratory mills.

The mean particle size of the polymer particles removed as the product fraction is preferably at least 200 μm, more preferably from 250 to 600 μm, very particularly from 300 to 500 μm. The mean particle size of the product fraction may be determined by means of EDANA recommended test method No. WSP 220.2-05 “Particle Size Distribution”, where the proportions by mass of the screen fractions are plotted in cumulative form and the mean particle size is determined graphically. The mean particle size here is the value of the mesh size which gives rise to a cumulative 50% by weight.

The proportion of particles with a particle size of at least 150 μm is preferably at least 90% by weight, more preferably at least 95% by weight, most preferably at least 98% by weight.

Polymer particles with too small a particle size lower the permeability (SFC). The proportion of excessively small polymer particles (“fines”) should therefore be small.

Excessively small polymer particles are therefore typically removed and recycled into the process. This is preferably done before, during or immediately after the polymerization, i.e. before the drying of the polymer gel. The excessively small polymer particles can be moistened with water and/or aqueous surfactant before or during the recycling.

It is also possible in later process steps to remove excessively small polymer particles, for example after the surface postcrosslinking or another coating step. In this case, the excessively small polymer particles recycled are surface postcrosslinked or coated in another way, for example with fumed silica.

When a kneading reactor is used for polymerization, the excessively small polymer particles are preferably added during the last third of the polymerization.

When the excessively small polymer particles are added at a very early stage, for example actually to the monomer solution, this lowers the centrifuge retention capacity (CRC) of the resulting water-absorbing polymer particles. However, this can be compensated, for example, by adjusting the amount of crosslinker b) used.

When the excessively small polymer particles are added at a very late stage, for example not until an apparatus connected downstream of the polymerization reactor, for example to an extruder, the excessively small polymer particles can be incorporated into the resulting polymer gel only with difficulty. Insufficiently incorporated, excessively small polymer particles are, however, detached again from the dried polymer gel during the grinding, are therefore removed again in the course of classification and increase the amount of excessively small polymer particles to be recycled.

The proportion of particles having a particle size of at most 850 μm is preferably at least 90% by weight, more preferably at least 95% by weight, most preferably at least 98% by weight.

The proportion of particles having a particle size of at most 600 μm is preferably at least 90% by weight, more preferably at least 95% by weight, most preferably at least 98% by weight.

Polymer particles with too great a particle size lower the swell rate. The proportion of excessively large polymer particles should therefore likewise be small.

Excessively large polymer particles are therefore typically removed and recycled into the grinding of the dried polymer gel.

To improve the properties, the polymer particles can be thermally surface postcrosslinked in a further process step v). Suitable surface postcrosslinkers are compounds which comprise groups which can form covalent bonds with at least two carboxylate groups of the polymer particles. Suitable compounds are, for example, polyfunctional amines, polyfunctional amidoamines, polyfunctional epoxides, as described in EP 0 083 022 A2, EP 0 543 303 A1 and EP 0 937 736 A2, di- or polyfunctional alcohols, as described in DE 33 14 019 A1, DE 35 23 617 A1 and EP 0 450 922 A2, or β-hydroxyalkylamides, as described in DE 102 04 938 A1 and U.S. Pat. No. 6,239,230.

Additionally described as suitable surface postcrosslinkers are cyclic carbonates in DE 40 20 780 C1, 2-oxazolidone and its derivatives, such as 2-hydroxyethyl-2-oxazolidone in DE 198 07 502 A1, bis- and poly-2-oxazolidinones in DE 198 07 992 C1, 2-oxotetrahydro-1,3-oxazine and its derivatives in DE 198 54 573 A1, N-acyl-2-oxazolidones in DE 198 54 574 A1, cyclic ureas in DE 102 04 937 A1, bicyclic amide acetals in DE 103 34 584 A1, oxetanes and cyclic ureas in EP 1 199 327 A2 and morpholine-2,3-dione and its derivatives in WO 2003/031482 A1.

Preferred surface postcrosslinkers are ethylene carbonate, ethylene glycol diglycidyl ether, reaction products of polyamides with epichlorohydrin, and mixtures of propylene glycol and 1,4-butanediol.

Very particularly preferred surface postcrosslinkers are 2-hydroxyethyloxazolidin-2-one, oxazolidin-2-one and 1,3-propanediol.

In addition, it is also possible to use surface postcrosslinkers which comprise additional polymerizable ethylenically unsaturated groups, as described in DE 37 13 601 A1.

The amount of surface postcrosslinkers is preferably 0.001 to 2% by weight, more preferably 0.02 to 1% by weight, most preferably 0.05 to 0.2% by weight, based in each case on the polymer particles.

In a preferred embodiment of the present invention, polyvalent cations are applied to the particle surface in addition to the surface postcrosslinkers before, during or after the surface postcrosslinking.

The polyvalent cations usable in the process according to the invention are, for example, divalent cations such as the cations of zinc, magnesium, calcium, iron and strontium, trivalent cations such as the cations of aluminum, iron, chromium, rare earths and manganese, tetravalent cations such as the cations of titanium and zirconium. Possible counterions are chloride, bromide, sulfate, hydrogensulfate, carbonate, hydrogencarbonate, nitrate, phosphate, hydrogenphosphate, dihydrogenphosphate and carboxylate, such as acetate and lactate. Aluminum sulfate and aluminum lactate are preferred. Apart from metal salts, it is also possible to use polyamines as polyvalent cations.

The amount of polyvalent cation used is, for example, 0.001 to 1.5% by weight, preferably 0.005 to 1% by weight, more preferably 0.02 to 0.8% by weight, based in each case on the polymer particles.

The surface postcrosslinking is typically performed in such a way that a solution of the surface postcrosslinker is sprayed onto the dried polymer particles. After the spraying, the polymer particles coated with surface postcrosslinker are dried thermally, and the surface postcrosslinking reaction can take place either before or during the drying.

The spray application of a solution of the surface postcrosslinker is preferably performed in mixers with moving mixing tools, such as screw mixers, disk mixers and paddle mixers. Particular preference is given to horizontal mixers such as paddle mixers, very particular preference to vertical mixers. The distinction between horizontal mixers and vertical mixers is made by the position of the mixing shaft, i.e. horizontal mixers have a horizontally mounted mixing shaft and vertical mixers a vertically mounted mixing shaft. Suitable mixers are, for example, horizontal Pflugschar® mixers (Gebr. Lödige Maschinenbau GmbH; Paderborn; Germany), Vrieco-Nauta continuous mixers (Hosokawa Micron BV; Doetinchem; the Netherlands), Processall Mixmill mixers (Processall Incorporated; Cincinnati; US) and Schugi Flexomix® (Hosokawa Micron BV; Doetinchem; the Netherlands). However, it is also possible to spray on the surface postcrosslinker solution in a fluidized bed.

The surface postcrosslinkers are typically used in the form of an aqueous solution. The content of nonaqueous solvent and/or total amount of solvent can be used to adjust the penetration depth of the surface postcrosslinker into the polymer particles.

When exclusively water is used as the solvent, a surfactant is advantageously added. This improves the wetting performance and reduces the tendency to form lumps. However, preference is given to using solvent mixtures, for example isopropanol/water, 1,3-propanediol/water and propylene glycol/water, where the mixing ratio by mass is preferably from 20:80 to 40:60.

The thermal surface postcrosslinking is preferably carried out in contact driers, more preferably paddle driers, most preferably disk driers. Suitable driers are, for example, Hosokawa Bepex® horizontal paddle driers (Hosokawa Micron GmbH; Leingarten; Germany), Hosokawa Bepex® disk driers (Hosokawa Micron GmbH; Leingarten; Germany) and Nara paddle driers (NARA Machinery Europe; Frechen; Germany). Moreover, it is also possible to use fluidized bed driers.

The thermal surface postcrosslinking can be effected in the mixer itself, by heating the jacket or blowing in warm air. Equally suitable is a downstream drier, for example a shelf drier, a rotary tube oven or a heatable screw. It is particularly advantageous to mix and dry in a fluidized bed drier.

Preferred surface postcrosslinking temperatures are in the range of 100 to 250° C., preferably 120 to 220° C., more preferably 130 to 210° C., most preferably 150 to 200° C. The preferred residence time at this temperature in the reaction mixer or drier is preferably at least 10 minutes, more preferably at least 20 minutes, most preferably at least 30 minutes, and typically at most 60 minutes.

Subsequently, the surface postcrosslinked polymer particles can be classified again, excessively small and/or excessively large polymer particles being removed and recycled into the process.

To further improve the properties, the surface postcrosslinked polymer particles can be coated or remoisturized.

The remoisturizing is carried out preferably at 30 to 80° C., more preferably at 35 to 70° C. and most preferably at 40 to 60° C. At excessively low temperatures, the water-absorbing polymer particles tend to form lumps, and, at higher temperatures, water already evaporates noticeably. The amount of water used for remoisturizing is preferably from 1 to 10% by weight, more preferably from 2 to 8% by weight and most preferably from 3 to 5% by weight. The remoisturizing increases the mechanical stability of the polymer particles and reduces their tendency to static charging.

Suitable coatings for improving the swell rate and the permeability (SFC) are, for example, inorganic inert substances, such as water-insoluble metal salts, organic polymers, cationic polymers and di- or polyvalent metal cations. Suitable coatings for dust binding are, for example, polyols. Suitable coatings for counteracting the undesired caking tendency of the polymer particles are, for example, fumed silica, such as Aerosil® 200, and surfactants, such as Span® 20.

The present invention further provides the water-absorbing polymer particles obtainable by the process according to the invention.

The present invention further provides water-absorbing polymer particles comprising a') at least one polymerized ethylenically unsaturated monomer a) which bears acid groups and may be at least partly neutralized, b') at least one polymerized crosslinker b), c') optionally one or more ethylenically unsaturated monomers d) copolymerized with the monomers mentioned under a) and d') optionally one or more water-soluble polymers e), said water-absorbing polymer particles comprising at least one aliphatic aldehyde or reaction product thereof with an aliphatic alcohol, an aliphatic amine, ammonia, a hypophosphite or a phosphite, it being possible to use the abovementioned aliphatic aldehydes or reaction products thereof with an aliphatic alcohol, an aliphatic amine, ammonia, a hypophosphite or a phosphite in the amount mentioned above.

In a preferred embodiment, the inventive polymer particles have been coated with at least one aliphatic aldehyde or reaction product thereof with an aliphatic alcohol, an aliphatic amine, ammonia, a hypophosphite or a phosphite.

The coating involves mixing the aliphatic aldehyde or reaction product thereof with an aliphatic alcohol, an aliphatic amine, ammonia, a hypophosphite or a phosphite, for example, with the polymer gel after step i), preferably with the polymer particles after step iv), and before, during or after step v), which gives a concentration gradient in the water-absorbing polymer particles.

The inventive water-absorbing polymer particles may additionally comprise a sulfite or be coated with a sulfite, it being possible to use the sulfites mentioned above in the amounts mentioned above.

The water-absorbing polymer particles produced by the process according to the invention have a centrifuge retention capacity (CRC) of typically at least 15 g/g, preferably at least 20 g/g, preferentially at least 22 g/g, more preferably at least 24 g/g, most preferably at least 26 g/g. The centrifuge retention capacity (CRC) of the water-absorbing polymer particles is typically less than 60 g/g. The centrifuge retention capacity (CRC) is determined by EDANA recommended test method No. WSP 241.2-05 "Centrifuge Retention Capacity".

The water-absorbing polymer particles produced by the process according to the invention have an absorption under a pressure of 49.2 $g/cm^2$ of typically at least 15 g/g, preferably at least 20 g/g, preferentially at least 22 g/g, more preferably at least 24 g/g, most preferably at least 26 g/g. The absorption under a pressure of 49.2 g/cm$^2$ of the water-absorbing polymer particles is typically less than 35 g/g. The absorption under a pressure of 49.2 g/cm$^2$ is determined analogously to EDANA recommended test method No. WSP 242.2-05 "Absorption under Pressure", except that a pressure of 49.2 g/cm$^2$ is established instead of a pressure of 21.0 g/cm$^2$.

The present invention further provides hygiene articles comprising inventive water-absorbing polymer particles, especially hygiene articles for feminine hygiene, hygiene articles for light and heavy incontinence, or small animal litter.

The hygiene articles typically comprise a water-impervious backside, a water-pervious topside and, in between, an absorbent core composed of the inventive water-absorbing polymer particles and fibers, preferably cellulose. The proportion of the inventive water-absorbing polymer particles in the absorbent core is preferably 20 to 100% by weight, more preferably 50 to 100% by weight.

The water-absorbing polymer particles are tested by means of the test methods described hereinafter.

The standard test methods designated "WSP" are described in: "Standard Test Methods for the Nonwovens Industry", 2005 edition, jointly published by the "Worldwide Strategic Partners" EDANA (Avenue Eugène Plasky 157, 1030 Brussels, Belgium, www.edana.org) and INDA (1100 Crescent Green, Cary, N.C. 27518, U.S.A., www.inda.org). This publication is obtainable both from EDANA and from INDA.

Methods:

The measurements should, unless stated otherwise, be carried out at an ambient temperature of 23±2° C. and a relative air humidity of 50±10%. The water-absorbing polymer particles are mixed thoroughly before the measurement.

Centrifuge Retention Capacity

The centrifuge retention capacity (CRC) is determined by EDANA recommended test method No. WSP 241.2-05 "Centrifuge Retention Capacity".

Absorption Under a Pressure of 49.2 g/cm$^2$

The absorption under a pressure of 49.2 g/cm$^2$ (AUL0.7 psi) is determined analogously by EDANA recommended test method No. WSP 242.2-05 "Absorption under Pressure", except that a pressure of 49.2 g/cm$^2$ (AUL0.7 psi) is established instead of a pressure of 21.0 g/cm$^2$ (AUL0.3 psi).

Saline Flow Conductivity

The saline flow conductivity (SFC) of a swollen gel layer under a pressure of 0.3 psi (2070 Pa) is determined, as described in EP 0 640 330 A1, as the gel layer permeability of a swollen gel layer of water-absorbing polymer particles, the apparatus described in the aforementioned patent application on page 19 and in FIG. 8 having been modified to the effect that the glass frit (40) is not used, the plunger (39) consists of the same polymer material as the cylinder (37) and now comprises 21 bores of equal size distributed homogeneously over the entire contact area. The procedure and evaluation of the measurement remain unchanged from EP 0 640 330 A1. The flow is detected automatically.

The saline flow conductivity (SFC) is calculated as follows:

$$\mathrm{SFC}[\mathrm{cm}^3\mathrm{s/g}]=(Fg(t=0)\times L0)/(d\times A\times WP)$$

where Fg(t=0) is the flow of NaCl solution in g/s, which is obtained with reference to a linear regression analysis of the Fg(t) data of the flow determinations by extrapolation to t=0, L0 is the thickness of the gel layer in cm, d is the density of the NaCl solution in g/cm$^3$, A is the area of the gel layer in cm$^3$ and WP is the hydrostatic pressure over the gel layer in dyn/cm$^2$.

Gel Bed Permeability

The gel bed permeability (GBP) of a swollen gel layer under a pressure of 0.3 psi (2070 Pa) is determined, as described in US 2005/02567575 (paragraphs [0061] and [0075]), as the gel bed permeability of a swollen gel layer of water-absorbing polymer particles.

CIE Color Number (L, a, b)

The color analysis is carried out according to the CIELAB method (Hunterlab, Volume 8, 1996, Book 7, pages 1 to 4) with a "LabScan XE S/N LX17309" colorimeter (HunterLab, Reston, US). This method describes the colors via the coordinates L, a and b of a three-dimensional system. L indicates the brightness, where L=0 means black and L=100 white. The values of a and b indicate the positions of the color on the red/green and yellow/blue color axes respectively, where +a represents red, −a represents green, +b represents yellow and −b represents blue. The HC60 value is calculated by the formula HC60=L−3b.

The color measurement corresponds to the three-area method according to DIN 5033-6.

Aging Test

Measurement 1 (initial color): A plastic dish of internal diameter 9 cm is overfilled with superabsorbent particles which are then smoothed flat with a blade over the edge, and the CIE color numbers and the HC60 value are determined.

Measurement 2 (after aging): A plastic dish of internal diameter 9 cm is overfilled with superabsorbent particles which are then smoothed flat with a blade over the edge. The dish is then placed open into a climate-controlled cabinet heated to 60° C. with constant relative air humidity of 86%. After 21 days have passed, the dish is taken out. After cooling to room temperature, the CIE color numbers and the HC60 value are determined again.

EXAMPLES

Example 1

HySorb® B 7055 (BASF SE; Ludwigshafen; Germany) was coated in a Pflugschar® M5 mixer (Gebr. Lödige Maschinenbau GmbH; Paderborn; Germany) at 23° C. and a shaft speed of 250 revolutions per minute, by means of a two-substance spray nozzle, with 1.0% by weight of a 10% by weight solution of sodium glyoxylate in demineralized water. The spray application was followed by mixing at a shaft speed of 80 revolutions per minute for another 15 minutes. The product obtained was screened off to a particle size of less than 850 μm.

Example 2

HySorb® B 7055 (BASF SE; Ludwigshafen; Germany) was coated in a Pflugschar® M5 mixer (Gebr. Lödige Maschinenbau GmbH; Paderborn; Germany) at 23° C. and a shaft speed of 250 revolutions per minute, by means of a two-substance spray nozzle, with 1.0% by weight of a 10% by weight solution of glyoxylic acid in demineralized water. The spray application was followed by mixing at a shaft speed of 80 revolutions per minute for another 15 minutes. The product obtained was screened off to a particle size of less than 850 μm.

Example 3

HySorb® B 7055 (BASF SE; Ludwigshafen; Germany) was coated in a Pflugschar® M5 mixer (Gebr. Lödige Maschinenbau GmbH; Paderborn; Germany) at 23° C. and a shaft speed of 250 revolutions per minute, by means of a two-substance spray nozzle, with 2% by weight of a mixture of 5% by weight of 2,5-dihydroxy-1,4-dioxane, 70% by weight of demineralized water and 25% by weight of isopropanol. The spray application was followed by mixing at a shaft speed of 80 revolutions per minute for another 15 minutes. The product obtained was dried in a vacuum drying cabinet at 80° C. and 250 mbar for 60 minutes and screened off to a particle size of less than 850 μm.

Example 4

HySorb® B 7055 (BASF SE; Ludwigshafen; Germany) was coated in a Pflugschar® M5 mixer (Gebr. Lödige Maschinenbau GmbH; Paderborn; Germany) at 23° C. and a shaft speed of 250 revolutions per minute, by means of a two-substance spray nozzle, with 2% by weight of a mixture of 5% by weight of 3,6-dihydroxy-1,4-dioxane-2,5-dimethanol, 60% by weight of demineralized water and 35% by weight of ethanol. The spray application was followed by mixing at a shaft speed of 80 revolutions per minute for another 15 minutes. The product obtained was dried in a vacuum drying cabinet at 80° C. and 250 mbar for 60 minutes and screened off to a particle size of less than 850 μm.

Example 5

HySorb® B 7055 (BASF SE; Ludwigshafen; Germany) was coated in a Pflugschar® M5 mixer (Gebr. Lödige Maschinenbau GmbH; Paderborn; Germany) at 23° C. and a shaft speed of 250 revolutions per minute, by means of a two-substance spray nozzle, with 1.0% by weight of a 10% by weight solution of hexamethylenetetramine in demineralized water. The spray application was followed by mixing at a shaft speed of 80 revolutions per minute for another 15 minutes. The product obtained was screened off to a particle size of less than 850 μm.

The water-absorbing polymer particles coated in examples 1 to 5 were subjected to the aging test. The results are compiled in table 1. The examples show that the inventive water-absorbing polymer particles are significantly lighter-colored and less discolored after aging.

The water-absorbing polymer particles of the HySorb® B 7055 type used in examples 1 to 5 had a CIE color number of L=93.4, a=3.7 and b=4.8, and an HC60 value of 79.1. HySorb® B 7055 are commercial surface postcrosslinked water-absorbing polymer particles.

TABLE 1

| Addition after surface postcrosslinking | | | | |
|---|---|---|---|---|
| | L | a | b | HC 60 |
| HySorb ® B 7055 | 64.8 | 4.8 | 17.8 | 11.5 |
| Ex. 1 | 82.1 | 1.2 | 11.1 | 48.8 |
| Ex. 2 | 82.6 | 0.9 | 10.8 | 50.2 |
| Ex. 3 | 79.6 | 1.4 | 11.6 | 44.8 |
| Ex. 4 | 80.2 | 1.3 | 11.9 | 44.5 |
| Ex. 5 | 78.4 | 1.7 | 12.1 | 42.1 |

Example 6

Production of Water-Absorbing Polymer Particles

A 2 l stainless steel beaker was initially charged with 326.7 g of 50% by weight sodium hydroxide solution and 675 g of frozen demineralized water. 392.0 g of acrylic acid were added while stirring, in the course of which the rate of addition was adjusted such that the temperature did not exceed 35° C. The mixture was then cooled with the aid of a cooling bath while stirring. Once the temperature of the mixture had fallen to 20° C., 1.08 g of triply ethoxylated glycerol triacrylate, 0.041 g of 2-hydroxy-2-methyl-1-phenylpropan-1-one (DAROCUR®1173; Ciba Specialty Chemicals Inc.; Basle; Switzerland) and 0.014 g of 2,2-dimethoxy-1,2-diphenylethan-1-one (IRGACURE® 651; Ciba Specialty Chemicals Inc.; Basle; Switzerland) were added. Cooling was continued and, on attainment of 15° C., the mixture was freed of oxygen by passing nitrogen through by means of a glass frit. On attainment of 0° C., 0.51 g of sodium persulfate (dissolved in 5 ml of demineralized water) and 0.2 g of 30% by weight hydrogen peroxide solution (dissolved in 6 ml of demineralized water) were added, and the monomer solution was transferred to a glass dish. The dimensions of the glass dish were such that a layer thickness of the monomer solution of 5 cm was established. Subsequently, 0.047 g of mixture of the sodium salt of 2-hydroxy-2-sulfinatoacetic acid, the disodium salt of 2-hydroxy-2-sulfonatoacetic acid and sodium bisulfite (Brüggolite® FF6; Brüggemann Chemicals; Heilbronn; Germany), dissolved in 5 ml of demineralized water, was added and the monomer solution was stirred briefly with the aid of a glass rod. The glass dish containing the monomer solution was placed under a UV lamp (UV intensity=25 mW/cm$^2$), in the course of which polymerization set in. After 16 minutes, the resulting polymer gel was extruded three times with the aid of a commercial meat grinder with a 6 mm perforated plate, and dried in a forced air drying cabinet at 160° C. for one hour. The dried polymer gel was then ground and screened off to a particle size of 150 to 850 μm.

For surface postcrosslinking, this base polymer was coated in a Pflugschar® M5 mixer with a heating jacket (Gebr. Lödige Maschinenbau GmbH; Paderborn; Germany) at 23° C. and a shaft speed of 450 revolutions per minute, by means of a two-substance spray nozzle, with a mixture of 0.10% by weight of ethylene glycol diglycidyl ether (Denacol® EX-810; Nagase ChemteX Corporation; Osaka; Japan), 1.50% by weight of 1,2-propanediol, 2.8% by weight of demineralized water and 0.4% by weight of aqueous aluminum sulfate solution (26.8% strength by weight), based in each case on the base polymer.

After the spray application, the product temperature was increased to 150° C. and the reaction mixture was kept at this temperature and at a shaft speed of 80 revolutions per minute for 60 minutes. The resulting product was allowed to cool again to ambient temperature and screened. The surface postcrosslinked water-absorbing polymer particles were screened off to a particle size of 150 μm to 850 μm and had the following properties:

CRC=31.6 g/g

AUL0.7 psi=22.9 g/g

SFC=25×10$^{-7}$ cm$^3$s/g

GBP=15 darcies

The resulting water-absorbing polymer particles had a CIE color number of L=88.7, a=−0.4 and b=9.0, and a HC60 value of 61.7.

Example 7

The procedure was as in example 6. Before the extrusion of the polymer gel, 0.20 g of glyoxylic acid was added.

Example 8

The procedure was as in example 6. Before the extrusion of the polymer gel, 0.30 g of potassium glyoxylate was added.

Example 9

The procedure was as in example 6. Before the extrusion of the polymer gel, 1.2 g of glyceraldehyde was added.

The water-absorbing polymer particles produced in examples 6 to 9 were subjected to the aging test. The results are compiled in table 2. The examples show that even small amounts of the aldehyde stabilize the inventive water-absorbing polymer particles against discoloration in the course of aging.

TABLE 2

| | Addition after polymerization | | | |
|---|---|---|---|---|
| | L | a | b | HC 60 |
| Ex. 6 (comp.) | 68.1 | 3.0 | 13.2 | 28.5 |
| Ex. 7 | 81.5 | 1.4 | 11.2 | 47.9 |
| Ex. 8 | 82.4 | 0.8 | 10.4 | 51.2 |
| Ex. 9 | 79.7 | 1.3 | 11.0 | 46.7 |

Example 10

Production of Water-Absorbing Polymer Particles 14.3 kg of aqueous sodium acrylate solution (37.5% strength by weight), 1.4 kg of acrylic acid and 350 g of demineralized water were mixed with 8.5 g of triply ethoxylated glycerol triacrylate. This solution was dropletized in a heated dropletizing tower filled with a nitrogen atmosphere (180° C., height 12 m, diameter 2 m, gas velocity 0.1 m/s in cocurrent, dropletizer of diameter 40 mm, internal height 2 mm and a dropletizer plate with 60 bores each of diameter 200 μm) at a metering rate of 32 kg/h. The temperature of the solution was 25° C. Just upstream of the dropletizer, the monomer solution was mixed with two initiator solutions by means of a static mixer. The initiator 1 used was a 3% by weight solution of 2,2'-azobis[2-(2-imidazolin-2-yl)propane] dihydrochloride in demineralized water, and the initiator 2 used was a 6.1% by weight solution of sodium peroxodisulfate in demineralized water. The metering rate of initiator solution 1 was 0.932 kg/h and the metering rate of initiator solution 2 was 0.629 kg/h. The polymer particles obtained were screened off to a particle size of 150 to 850 μm in order to remove any agglomerates formed, and had the following properties:

CRC=30.4 g/g

AUL0.7 psi=22.9 g/g

SFC=$24\times10^{-7}$ $cm^3s/g$

GBP=8 darcies

The resulting water-absorbing polymer particles had a CIE color number of L=93.1, a=0.5 and b=3.2, and an HC60 value of 83.5.

Example 11

Production of Water-Absorbing Polymer Particles 14.3 kg of aqueous sodium acrylate solution (37.5% strength by weight), 1.4 kg of acrylic acid and 350 g of demineralized water were mixed with 8.5 g of triply ethoxylated glycerol triacrylate. This solution was dropletized in a heated dropletizing tower filled with a nitrogen atmosphere (180° C., height 12 m, diameter 2 m, gas velocity 0.1 m/s in cocurrent, dropletizer of diameter 40 mm, internal height 2 mm and a dropletizer plate with 60 bores each of diameter 200 μm) at a metering rate of 32 kg/h. The temperature of the solution was 25° C. Just upstream of the dropletizer, the monomer solution was mixed with three initiator solutions by means of a static mixer. The initiator 1 used was a 3% by weight solution of 2,2'-azobis[2-(2-imidazolin-2-yl) propane]dihydrochloride in demineralized water, the initiator 2 used was a 6.1% by weight solution of sodium peroxodisulfate in demineralized water, and the initiator 3 used was a 3% by weight solution of the disodium salt of 2-hydroxy-2-sulfonatoacetic acid in deionized water. The metering rate of initiator solution 1 was 0.548 kg/h, the metering rate of initiator solution 2 was 0.449 kg/h and the metering rate of solution 3 was 0.183 kg/h. The polymer particles obtained were screened off to a particle size of 150 to 850 μm in order to remove any agglomerates formed, and had the following properties:

CRC=31.8 g/g

AUL0.7 psi=22.5 g/g

SFC=$19\times10^{-7}$ $cm^3s/g$

GBP=7 darcies

The resulting water-absorbing polymer particles had a CIE color number of L=93.6, a=0.4 and b=2.7, and an HC60 value of 85.5.

Example 12

1000 g of the water-absorbing polymer particles from example 10 were coated in a Pflugschar® M5 mixer (Gebr. Lödige Maschinenbau GmbH; Paderborn; Germany) at 23° C. and a shaft speed of 250 revolutions per minute, by means of two two-substance spray nozzles, simultaneously with a solution of 1.5 g of sodium glyoxylate in 15 g of demineralized water and with a solution of 1.9 g of sodium bisulfite in 15 g of demineralized water. The spray application was followed by mixing at a shaft speed of 80 revolutions per minute for another 15 minutes. The resulting product was screened off to a particle size of less than 850 μm.

Example 13

1000 g of the water-absorbing polymer particles from example 10 were coated in a Pflugschar® M5 mixer (Gebr. Lödige Maschinenbau GmbH; Paderborn; Germany) at 23° C. and a shaft speed of 250 revolutions per minute, by means of two two-substance spray nozzles, simultaneously with a solution of 1.5 g of sodium glyoxylate in 15 g of demineralized water and with a solution of 4.5 g of sodium bisulfite in 20 g of demineralized water. The spray application was followed by mixing at a shaft speed of 80 revolutions per minute for another 15 minutes. The resulting product was screened off to a particle size of less than 850 μm.

Example 14

1000 g of the water-absorbing polymer particles from example 10 were coated in a Pflugschar® M5 mixer (Gebr. Lödige Maschinenbau GmbH; Paderborn; Germany) at 23° C. and a shaft speed of 250 revolutions per minute, by means of two two-substance spray nozzles, simultaneously with a solution of 1.5 g of sodium glyoxylate in 15 g of demineralized water and with a solution of 0.8 g of sodium bisulfite in 10 g of demineralized water. The spray application was followed by mixing at a shaft speed of 80 revolutions per minute for another 15 minutes. The resulting product was screened off to a particle size of less than 850 μm.

Example 15

1000 g of the water-absorbing polymer particles from example 11 were admixed in a Pflugschar® M5 mixer (Gebr.

Lödige Maschinenbau GmbH; Paderborn; Germany) at 23° C. and a shaft speed of 80 revolutions per minute with 1.5 g of a hydrophobic precipitated silica (Sipernat® D-17; Evonik Degussa GmbH; Frankfurt am Main; Germany). After a mixing time of 5 minutes, the shaft speed was increased to 250 revolutions per minute and, by means of a two-substance spray nozzle, a solution of 0.4 g of glyoxylic acid in 20 g of demineralized water was applied. The spray application was followed by mixing at a shaft speed of 80 revolutions per minute for another 15 minutes. The resulting product was screened off to a particle size of less than 850 μm.

The water-absorbing polymer particles produced in examples 10 to 15 were subjected to the aging test. The results are compiled in table 3. The examples show that the inventive water-absorbing polymer particles, after aging, are significantly lighter-colored and less discolored.

TABLE 3

| addition after the drying | | | | |
|---|---|---|---|---|
| | L | a | b | HC 60 |
| Ex. 10 (comp.) | 70.4 | 3.9 | 18.5 | 14.9 |
| Ex. 11 (comp.) | 75.2 | 2.8 | 14.0 | 33.2 |
| Ex. 12 | 79.6 | 1.2 | 11.9 | 43.9 |
| Ex. 13 | 80.2 | 1.4 | 11.6 | 45.4 |
| Ex. 14 | 80.0 | 1.3 | 11.9 | 44.3 |
| Ex. 15 | 85.7 | 0.4 | 8.7 | 59.6 |

Example 16

Production of Water-Absorbing Polymer Particles

A Pflugschar® VT 5R-MK paddle drier of capacity 5 l with a heating/cooling jacket (Gebr. Lödige Maschinenbau GmbH; Paderborn: Germany) was initially charged with 459 g of demineralized water, 213.9 g of acrylic acid, 1924.9 g of aqueous sodium acrylate solution (37.3% strength by weight) and 2.52 g of triply ethoxylated glycerol triacrylate, and inertized by sparging with nitrogen for 20 minutes. The shaft of the reactor was constantly rotated at 96 revolutions per minute. The reaction mixture was cooled from the outside such that the subsequent addition of initiator was effected at approx. 20° C. Finally, 2.139 g of sodium persulfate (dissolved in 12.12 g of demineralized water), 0.046 g of ascorbic acid (dissolved in 9.12 g of demineralized water) and 0.127 g of 30% by weight aqueous hydrogen peroxide solution (diluted with 1.15 g of demineralized water) were added in rapid succession to the Pflugschar® paddle drier while stirring. The reaction set in rapidly and, on attainment of an internal temperature of 30° C., the jacket was heated with heat carrier medium at 80° C. in order to conduct the reaction to the end under very substantially adiabatic conditions. On attainment of the maximum temperature, the mixture was cooled again (cooling liquid at −12° C.), such that the polymer gel formed was cooled to below 50° C. and then discharged. The polymer gel was then dried in a forced-air drying cabinet at 160° C. for one hour. The dried polymer gel was then ground and screened off to a particle size of 150 to 710 μm.

For surface postcrosslinking, this base polymer was coated in a Pflugschar® M5 mixer with a heating jacket (Gebr. Lödige Maschinenbau GmbH; Paderborn; Germany) at 23° C. and a shaft speed of 450 revolutions per minute, by means of a two-substance spray nozzle, with a mixture of 0.125% by weight of N-(2-hydroxyethyl)-2-oxazolidinone, 1.5% by weight of demineralized water, 1.5% by weight of 1,3-propanediol, 0.003% by weight of sorbitan monococoate (Span® 20) and 2.8% by weight of aqueous aluminum lactate solution (25% strength by weight), based in each case on the base polymer. After the spray application, the product temperature was increased to 175° C. and the reaction mixture was kept at this temperature and at a stirrer speed of 80 revolutions per minute for 80 minutes. The resulting product was allowed to cool again to ambient temperature and screened. The surface postcrosslinked water-absorbing polymer particles were screened off to a particle size of 150 to 710 μm.

The resulting water-absorbing polymer particles had a CIE color number of L=92.2, a=−0.4 and b=6.5, and an HC60 value of 72.2.

Example 17

The procedure was as in example 16. Before the polymerization, 1.2 g of sodium 2,2-dimethoxyacetate were initially charged in the Pflugschar® paddle drier.

Example 18

The procedure was as in example 16. The base polymer was additionally coated with 0.10% by weight of glyoxylic acid, based on the base polymer.

Example 19

The procedure was as in example 16. The base polymer was additionally coated with 0.15% by weight of sodium glyoxylate, based on the base polymer.

Example 20

The polymer prepared in example 16 was coated in a Pflugschar® M5 mixer (Gebr. Lödige Maschinenbau GmbH; Paderborn; Germany) at 23° C. and a shaft speed of 250 revolutions per minute, by means of a two-substance spray nozzle, with 1.5% by weight of a 10% by weight solution of 2-hydroxy-2-phosphonoacetic acid in demineralized water. The spray application was followed by mixing at a shaft speed of 80 revolutions per minute for another 15 minutes. The resulting product was screened off to a particle size of less than 850 μm.

The water-absorbing polymer particles produced in examples 16 to 20 were subjected to the aging test. The results are compiled in tables 4 and 5. The examples show that the inventive water-absorbing polymer particles are significantly lighter-colored and less discolored after aging, without the absorption properties being impaired.

TABLE 4

| Absorption properties | | | | |
|---|---|---|---|---|
| | CRC [g/g] | AUL0.7 psi [g/g] | SFC [$10^{-7}$ cm$^3$s/g] | GBP [darcies] |
| Ex. 16 (comp.) | 28.7 | 23.9 | 125 | 15 |
| Ex. 17 | 29.2 | 23.3 | 110 | 14 |
| Ex. 18 | 28.9 | 23.5 | 123 | 16 |
| Ex. 19 | 28.5 | 24.1 | 129 | 14 |
| Ex. 20 | 28.4 | 23.8 | 116 | 17 |

TABLE 5

| Addition before the polymerization or before or after the thermal surface postcrosslinking | | | | |
|---|---|---|---|---|
| | L | a | b | HC 60 |
| Ex. 16 (comp.) | 65.1 | 4.9 | 17.3 | 13.2 |
| Ex. 17 | 79.7 | 2.1 | 12.1 | 43.4 |
| Ex. 18 | 81.4 | 1.0 | 11.4 | 47.2 |
| Ex. 19 | 82.3 | 0.9 | 10.2 | 51.7 |
| Ex. 20 | 82.0 | 1.2 | 10.8 | 49.6 |

The invention claimed is:

1. A process for producing water-absorbing polymer particles by polymerizing a monomer solution or suspension comprising a) at least one ethylenically unsaturated monomer which bears acid groups and optionally is at least partly neutralized, b) at least one crosslinker, c) at least one initiator, d) optionally one or more ethylenically unsaturated monomer copolymerizable with the monomers mentioned under a); and e) optionally one or more water-soluble polymers, comprising the steps of polymerizing the monomer solution or suspension to give a polymer gel i), optionally comminuting the resulting polymer gel ii), drying the polymer gel iii), grinding and classifying the dried polymer gel to polymer particles iv), and optionally thermally surface postcrosslinking the classified polymer particles v), which comprises adding at least one aliphatic aldehyde or reaction product thereof with an aliphatic alcohol, an aliphatic amine, ammonia, a hypophosphite, or a phosphite before, during or after one of steps i) to v), wherein the aliphatic aldehyde or reaction product thereof with an aliphatic alcohol, an aliphatic amine, ammonia, a hypophosphite, or a phosphite is selected from the group consisting of formaldehyde, acetaldehyde, propionaldehyde, butyraldehyde, glycolaldehyde, glyceraldehyde, a formaldehyde acetal, an acetaldehyde acetal, a propionaldehyde acetal, a butyraldehyde acetal, a glycolaldehyde acetal, a glyceraldehyde acetal, sodium glyoxylate, potassium glyoxylate, 2,5-dihydroxy-1,4-dioxane, 3,6-dihydroxy-2,5-dihydroxymethyl-1,4-dioxane, sodium 2,2-dimethoxyacetate, potassium 2,2-dimethoxyacetate, sodium 2,2-diethoxyacetate, potassium 2,2-diethoxyacetate, hexamethylenetetramine, an azomethine, an enamine, an aminal, 2-hydroxy-2-phosphonoacetic acid, and 2-hydroxy-2-phosphonoacetic acid.

2. The process according to claim 1, wherein the aliphatic aldehyde or reaction product thereof with an aliphatic alcohol, an aliphatic amine, ammonia, a hypophosphite, or a phosphite is added after step iv) and before, during, or after step v).

3. The process according to claim 1, wherein the aliphatic aldehyde or reaction product thereof with an aliphatic alcohol, an aliphatic amine, ammonia, a hypophosphite, or a phosphite is added after step v).

4. The process according to claim 1, wherein the aliphatic aldehyde or reaction product thereof with an aliphatic alcohol, an aliphatic amine, ammonia, a hypophosphite, or a phosphite is selected from the group consisting of sodium glyoxylate, and potassium glyoxylate.

5. The process according to claim 1, wherein from 0.01 to 0.5% by weight of the aliphatic aldehyde or reaction product thereof with an aliphatic alcohol, an aliphatic amine, ammonia, a hypophosphite, or a phosphite, based on the water-absorbing polymer particles, is added.

6. The process according to claim 1, wherein a sulfite is additionally added.

7. The process according to claim 6, wherein the sulfite is selected from the group consisting of sodium hydrogen sulfite and potassium hydrogen sulfite.

8. The process according to claim 6, wherein from 0.01 to 1% by weight of the sulfite, based on the water-absorbing polymer particles, is added.

9. Water-absorbing polymer particles obtainable by a process according to claim 1.

10. Water-absorbing polymer particles comprising a') at least one polymerized ethylenically unsaturated monomer which bears acid groups and optionally is at least partly neutralized, b') at least one polymerized crosslinker, c') optionally one or more ethylenically unsaturated monomer copolymerized with the monomer mentioned under a'), and d') optionally one or more water-soluble polymers, said water-absorbing polymer particles comprising at least one aliphatic aldehyde or reaction product thereof with an aliphatic alcohol, an aliphatic amine, ammonia, a hypophosphite, or a phosphite, wherein the aliphatic aldehyde or reaction product thereof with an aliphatic alcohol, an aliphatic amine, ammonia, a hypophosphite, or a phosphite is selected from the group consisting of formaldehyde, acetaldehyde, propionaldehyde, butyraldehyde, glycolaldehyde, glyceraldehyde, a formaldehyde acetal, an acetaldehyde acetal, a propionaldehyde acetal, a butyraldehyde acetal, a glycolaldehyde acetal, a glyceraldehyde acetal, sodium glyoxylate, potassium glyoxylate, 2,5-dihydroxy-1,4-dioxane, 3,6-dihydroxy-2,5-dihydroxymethyl-1,4-dioxane, sodium 2,2-dimethoxyacetate, potassium 2,2-dimethoxyacetate, sodium 2,2-diethoxyacetate, potassium 2,2-diethoxyacetate, hexamethylenetetramine, an azomethine, an enamine, an aminal, 2-hydroxy-2-phosphonoacetic acid, and 2-hydroxy-2-phosphonoacetic acid.

11. Polymer particles according to claim 10, which have been coated with at least one aliphatic aldehyde or reaction product thereof with an aliphatic alcohol, an aliphatic amine, ammonia, a hypophosphite, or a phosphite.

12. Polymer particles according to claim 10, which additionally comprise a sulfite or have been coated with a sulfite.

13. Polymer particles according to claim 9, which have a centrifuge retention capacity of at least 15 g/g.

14. A hygiene article comprising water-absorbing polymer particles according to claim 10.

* * * * *